United States Patent [19]

Banks et al.

[11] Patent Number: 5,000,732
[45] Date of Patent: Mar. 19, 1991

[54] DEVICE AND METHOD FOR PROVIDING MULTIPLE DOSES OF A LIQUID MATERIAL OVER TIME TO A GUT ASSOCIATED LYMPHOID TISSUE OR A TEST ANIMAL

[75] Inventors: Ronald E. Banks, Ft. Meade; Michael Roy, Olney; Clayton Hadick, Rockville, all of Md.

[73] Assignee: The United States of America as represented by the Secretary of the Army, Washington, D.C.

[21] Appl. No.: 343,695

[22] Filed: Apr. 27, 1989

[51] Int. Cl.$^5$ .............................................. A61M 31/00
[52] U.S. Cl. ...................... 604/49; 604/175; 604/180; 604/280
[58] Field of Search ............ 604/890.1, 891.1, 8, 604/51, 93, 104, 116, 175, 180, 49, 280

[56] References Cited

U.S. PATENT DOCUMENTS

| | | | |
|---|---|---|---|
| 3,918,456 | 11/1975 | Patel | 604/104 |
| 4,534,760 | 8/1985 | Raible | 604/175 |
| 4,569,675 | 2/1986 | Prosl et al. | 604/175 |
| 4,692,146 | 9/1987 | Hilger | 604/93 |
| 4,699,611 | 10/1987 | Bowden | 604/51 |
| 4,756,707 | 7/1988 | MacLeod et al. | 604/93 |

Primary Examiner—John D. Yasko
Assistant Examiner—Adam J. Cermak
Attorney, Agent, or Firm—Werten F. W. Bellamy; Anthony T. Lane

[57] ABSTRACT

A simple, inexpensive construction, utilizing commonly available plastic tubing, hypodermic needle hub, suture materials and cyanoacrylic glue is provided for subcutaneous implantation within a test animal, one of the generally tubular structure being permanently affixed in communication with a selected portion of the gastrointestinal tract consisting essentially of the small intestines, colon, stomach or gut-associated lymphoid tissue (GALT) of the test animal, with the other end of the tubular structrure firmly located behind the head of the test animal for easy access thereto. This invention, following implantation thereof into a test animal, may be readily utilized for the controlled delivery therethrough of multiple doses of one or more selected liquid materials for direct delivery thereof to the gastrointestinal tract of the test animal.

16 Claims, 1 Drawing Sheet

DEVICE AND METHOD FOR PROVIDING MULTIPLE DOSES OF A LIQUID MATERIAL OVER TIME TO A GUT ASSOCIATED LYMPHOID TISSUE OR A TEST ANIMAL

The invention described herein may be manufactured, used and licensed by or for the Government for Governmental purposes without the payment to us of any royalties thereon.

FIELD OF THE INVENTION

This invention relates to a device and a method for providing multiple doses of a liquid material over an extended period of time to areas within the gastrointestinal tract such as the small intestines, colon, stomach or a gut-associated lymphoid tissue (GALT) of a test animal, and, more particularly, to such a device and method that facilitates the delivery of a variety of liquid materials directly to the gastrointestinal tract for periods extending many weeks of a physiologically normal, functioning test animal.

BACKGROUND OF THE INVENTION

Non-human primates are frequently used to test the efficacy and safety of new mucosal vaccines, i.e., vaccines that are most efficaciously applied directly to a mucosal membrane of a subject, but for various reasons, suitable primates that may have to be sacrificed at the end of a set of vaccine applications are very difficult to obtain and very expensive when available. Additionally, there is an increasingly strong public sentiment against the use of primates as test subjects. Because of such difficulties and expense, it is generally quite difficult to obtain statistically significant results to convincingly demonstrate the safety of a novel vaccine through the use of primates. Primate studies also tend to limit the flexibility of the investigations, e.g., because investigators are generally hesitant to modify or improve an imperfect vaccine for fear of having insufficient test animals to complete a credible study. In short, therefore, the lack of a suitable animal model for adequate testing of mucosal immunogens has resulted in this country in relatively limited testing or refinement of numerous candidate vaccines prior to clinical trials.

The rabbit appears to be an excellent test animal for such studies, not only because it is relatively small and easy to handle, relatively inexpensive to breed and hence commercially inexpensive to obtain, but also because it has a comparatively large mucosal immune system, a sensitive lower gastrointestinal tract and because rabbits have been used for mucosal immunization with satisfactory results and are therefore generally deemed by investigators to be a suitable animal model.

There are two broad categories of vaccine: those that are parentally administered by injection into muscle tissue and those which require mucosal administration, e.g., polio vaccine on a sugar cube. Parental vaccines, generally designed to stimulate systemic immune responses, are routinely tested in lower vertebrates such as mice, rats or rabbits and, only later, once the best candidates among the tested antigens are determined, are the vaccines tested in non-human primates and subsequently in humans. During the parental vaccine screening process in rodents or rabbits, systemic immune responses are measured and both local or systemic pathologic changes are noted.

The procedures suitable for testing of parental vaccine often are not followed in evaluating putative mucosal vaccines because mucosal immune responses are difficult to measure in small animals and because the number of experimental variables, e.g., the route of administration, the use of adjutants and the amount or form of the antigen, demand relatively large numbers of animals. As noted above, the rabbit is a suitable test animal for many reasons and the problem therefore resolves to one of obtaining safe, controlled and long term access to a suitably large portion of the animals' mucosal tissue for delivery thereto of liquid test materials.

Many studies have been performed with delivery of liquid materials to the intestinal mucosal tissues of rabbits by using a Thiry-Vella (T-V) loop system. This T-V system involves the surgical isolation and exteriorization of a section of the gut of the test animal. There are some significant disadvantages associated with use of the T-V system For example, data obtained through use of a T-V loop system has a very broad standard array, a consequence that is believed to be related to the modified physiological function of the intestine, e.g., Paneth cell hyperplasia, colonization with undesirable bacteria, and post-surgical intestinal inflammation. Furthermore, the so-called "T-V loop" is not truly a functional intestinal loop and, therefore, is not a very good model of a functioning physiologic system. Finally, mucus buildup within a T-V loop may restrict antigenic presentation to the lymphoid tissue, and one significant consequence of this is that there is a practical limitation in the usefulness of such T-V loops, usually less than 15 days For many sensitive studies, and especially to obtain a solid data base to justify the much more expensive follow-up studies needed in primates and human subjects, it is required that the test animal be available with a truly functional physiologic system to receive the liquid test materials for periods in excess of 15 days.

There is, therefore, a real need for a device and a method that will enable practitioners and researchers to deliver liquid test materials over a long period of time directly to a relatively large mucosal lymphoid tissue. e.g., in the lower gastrointestinal tract of the test animal, without undue expense of time or energy.

SUMMARY OF THE INVENTION

Accordingly, it is an object of this invention to provide a device that enables a user to deliver multiple doses of a liquid test material over an extended period of time to areas within the gastrointestinal tract, such as the small intestines, colon, stomach or a gut-associated lymphoid tissue (GALT) of a test animal.

It is the further object of this invention to provide a device that enables a user to controllably deliver over an extended period of time a plurality of liquid materials in selected order and in selected amounts to a gut-associated lymphoid tissue (GALT) of a test animal.

It is the further object of this invention to provide a device that enables a user to deliver multiple doses of one or more liquid materials over an extended period of time to a gut-associated lymphoid tissue (GALT) of a relatively inexpensive test animal while the GALT remains part of the test animal's functioning physiologic system.

It is a related object of this invention to provide a method for delivering multiple doses of a liquid material over an extended period of time to a gut-associated lymphoid tissue (GALT) of a test animal.

It is a further related object of this invention to provide a method for delivering multiple doses of one or more liquid test materials, in controlled manner over an extended period of time, to a gut-associated lymphoid tissue (GALT) of a test animal.

It is an even further object of this invention to provide a method by which multiple doses of one or more liquid materials can be controllably delivered over an extended period of time to a gut-associated lymphoid tissue (GALT) of a relatively inexpensive test animal while the GALT thereof remains a functioning part of the physiologic system of the test animal.

Such objects are realized in a first aspect of this invention by providing a device that allows delivery of multiple doses of a liquid test material over an extended period of time to a gut-associated lymphoid tissue (GALT) of a test animal, the device including a length of tubing formed to have a first end that is adapted to be fixed in communication with a portion of the test animal's GALT contained within the test animal's body and a second end of the tubing adapted for receiving a quantity of a liquid material for delivery through the tubing to the GALT, and means for affixing the first end in communication with the GALT with the second end disposed with respect to the test animal at a location that is readily accessible by the user of the device, but with the length of tubing between the tubing ends, as well as the second end, all being secured to be safe from dislocation by the test animal subsequent to attachment of the device in place on the test animal.

In another aspect of this invention, there is provided a method for delivering multiple doses of a liquid material over an extended period of time to a gut-associated lymphoid tissue (GALT) of a test animal, the method including the steps of affixing a first end of a length of tubing in communication with a selected portion of the GALT within the test animal, securing a second end of the length of tubing to the animal for ease of access thereto by the user of the device where it cannot be disturbed by the test animal, the length of tubing between the first and second ends being secured within the test animal, and flowing into the second end a dose of a liquid material for conveyance through the tubing and such first end to the GALT.

The above and still further objects, features and advantages of the present invention will become apparent upon consideration of the following detailed description of a specific embodiment thereof, especially when taken in conjunction with the accompanying drawings.

DESCRIPTION OF THE PREFERRED EMBODIMENT

Figure 1:
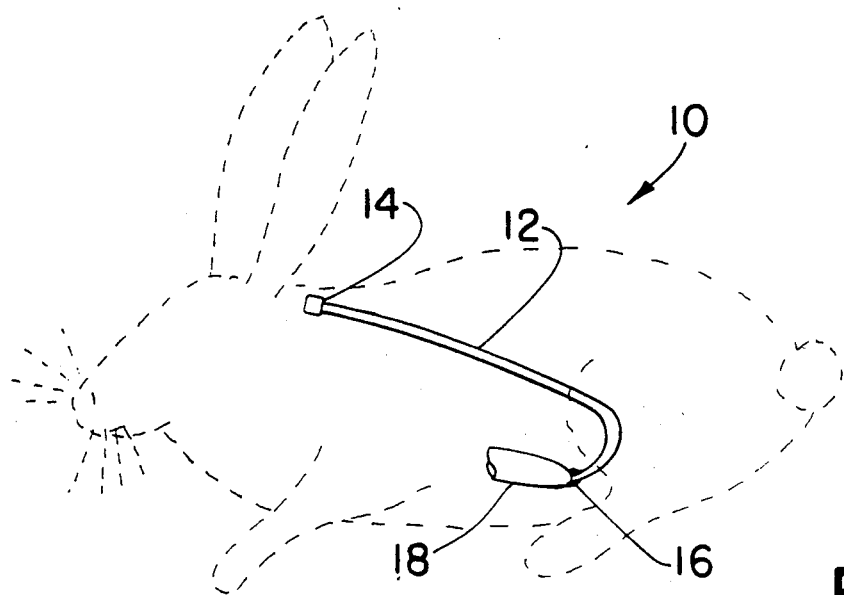
FIG. 1 is a side elevation view of a test animal, the length of tubing and both of its ends being shown in schematic form to illustrate the general disposition of the device with respect to the test animal.

The present invention is particularly suitable for mucosal administration of vaccines to intestinal lymphoid tissue in a rabbit, specifically to the appendix thereof. The manner in which the device is disposed with respect to a test rabbit is schematically indicated in FIG. 1. Use of the device in connection with the appendix of a test rabbit, however, is merely a preferred embodiment and use of the device. Persons skilled in the art will undoubtedly consider use of this device, perhaps with minor modifications, for use with other mucosal surfaces than that of a test animal's appendix and should be able to readily adapt the device in the method of its use to other test animals.

In the preferred embodiment of this invention, therefore, as best seen in FIG. 1, in a test animal 10, there is implanted beneath the animal's skin a length of tubing 12 which extends from a user-accessible liquid injection fitting 14 that is preferably mounted behind the test animal's head so that it may not be easily disturbed or removed by the test animal Tubing 12 is connected at a second end 16 to appendix 18 of the test animal as more fully described hereinafter.

As an initial matter depending upon the size of the test animal, approximately 40 cm. of polyethylene or polypropylene catheter tubing is sufficient, e.g., for adult rabbits as test animals. Thus, as best seen in FIG. 2, tubing 12 for such use would be approximately 40 cm. long between a first end 20, through which the liquid material is delivered to the test animal's mucosal tissue and a second end, 26, through which the liquid material is received in the tubing from fitting 14.

Figure 2:
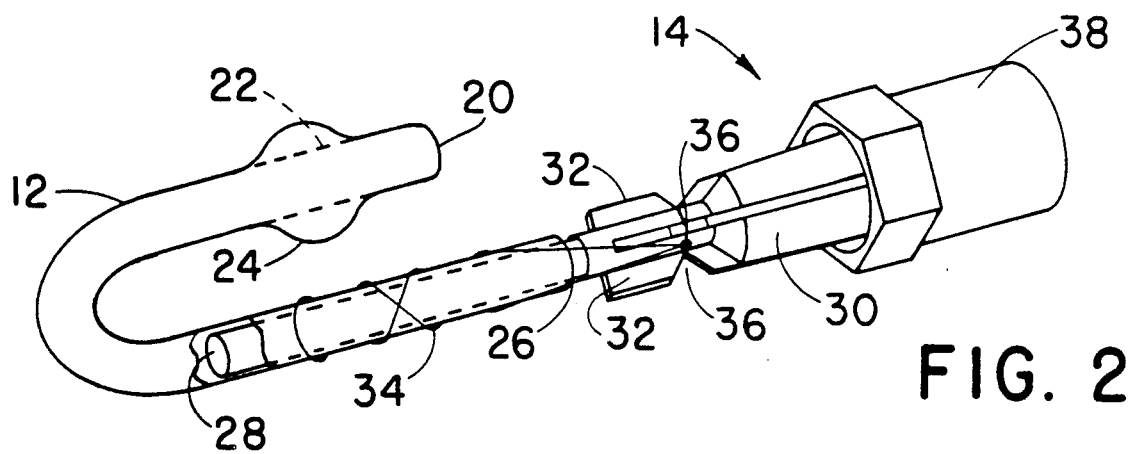
FIG. 2 is a partial perspective side view of the essential elements at both ends of the tubing according to a preferred embodiment of the present invention.
Figure 3:
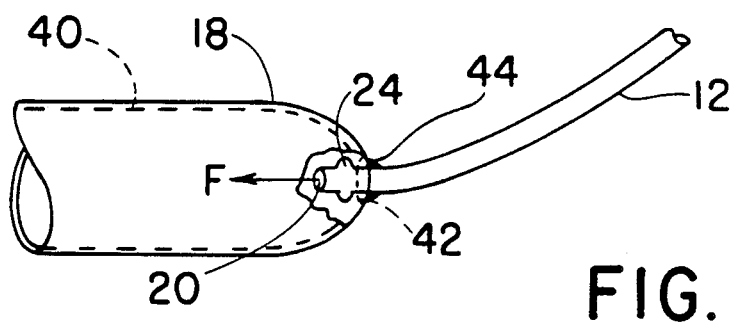
FIG. 3 is a partial view of one end of the device where it is permanently affixed to a portion of the test animal's gastrointestinal system, specifically at the distal end of the test animal's appendix, to illustrate the preferred manner of connecting the same.

As also best seen in FIG. 2, a short length 22 of the tubing immediately adjacent delivery end 20 is preferably enlarged to have a bulbous shape 24 that is smoothly contiguous with the rest of the tubing on both sides thereof. As best seen in FIG. 3, this bulbous portion 24, facilitates retention of the delivery end of tubing 12 within the test animal's appendix 18.

A principal object of this invention is to enable a user working only with materials readily available in most reasonably equipped biology labs, to assemble and utilize this invention. Polyethylene or polypropylene catheter tubing is readily available and, when portion 22 of the length 12 thereof is locally heated, e.g., by being held and turned slowly over a match flame or a flame from a cigarette lighter, the plastic material of the tubing will soften and shrink somewhat lengthwise while increasing its diameter to form a bulbous portion 24 as indicated in FIGS. 2 and 3. This takes but a few seconds and any excess length of tubing beyond bulbous portion 24 can be easily trimmed What is important is to obtain a smooth, contiguous surface extending from the bulk of the length 12 of tubing to bulbous portion 24 and to delivery end 20 immediately adjacent thereto.

Connection of the receiving end 26 of tubing 12 to fitting 14 is most immediately accomplished as follows, although other similar solutions will no doubt occur to persons skilled in the art. The sharp end of a conventional 20-gauge needle 28 is preferably cut off so that it has a blunt end and a needle length of between 10 and 11 mm. To make certain that tubing 12 near the end of needle 28 does not suffer abrasion or cuts, it is helpful to file the end of needle 28 so that the end is relatively smooth.

Such needles, normally used with sharp ends for hypodermic injection purposes, are available from a number of commercial sources and, typically, have a plastic hub 30 holding one end of the steel needle. Hub 30 is conventionally provided with a plurality of vanes 32 symmetrically disposed therearound. Since it is intended that the device according to this invention should remain implanted in the test animal for a period lasting for 90 days or longer, it is very important that receiving end 26 of tubing 12 not slip off needle 28. To ensure this, one simple solution available to the user is to tie a length of suture thread 34 tightly around tubing 12 where it covers needle 28 and, thereafter, to wrap the distal ends of suture thread 34 around and in a set of notches 36 cut in vanes 32, e.g., with a razor blade or pocket knife, to ensure that suture thread 34 does not come loose during use of the device. Heavy, nonabsorbable suture silk size O is particularly suitable for this purpose. Finally, a commercially available luer lock obturator 38 is then attached to needle hub 30.

To ensure against incidental and accidental infections of the test animal, the device which is now structurally complete is subjected, preferably, to ethylene oxide sterilization in readiness for implantation into the test animal.

Pasteurella-free New Zealand white rabbits, typically weighing approximately 3 kg., are suitable test animals for testing of mucosally administered vaccines, and the following description relates to the preparation of such a test animal for use of the device according to this invention.

The rabbit is fed a high fiber rabbit ration and provided with water ad libitum. In preparation for surgery, the rabbit is anesthetized by an intramuscular injection of xylazine (2 mg./kg.) and ketamine HCl (10 mg./kg.). Anesthesia is maintained with halothane delivered via a mask in an open circuit. The abdomen and interscapular regions are clipped free of fur and the rabbit is positioned on a warming table in dorsal recumbency, i.e., on its back. The abdominal skin is prepared using a standard three cycle approach of iodine detergent scrub and isopropyl alcohol, followed by a final spray with a tamed iodine solution. Sterile technique is used throughout the procedure to avoid incidental infections. An incision is made through the skin and linea alba, extending from the umbilicus caudally for 4.0–5.0 cm. A culture is taken of the abdominal cavity. The appendix is identified and a purse string suture, using 6–0 cardiovascular silk is established at the appendicular tip. An incision of the appendicular serosa is made within the purse string by inserting a 12 gauge needle into the appendix Approximately 1 cc of appendicular contents is withdrawn into a syringe for culture and organism identification and the needle is then removed from the appendix.

The distal end 20 of the tubing is inserted through the needle track and into the appendix 18, with the enlarged bulbous portion 24 carefully inserted into the appendix. Closure of the appendicular wall is then accomplished by tying a pre-placed purse string suture 42, best seen in FIG. 3, so that the appendicular tissue is drawn tightly around tubing 12 adjacent bulbous portion 24 thereof. A small quantity of surgical grade cyanoacrylic glue 44 is then applied to the appendicular serosa at the junction of tubing 12 and appendix 18. After a short lapse of time, to allow the deposit of cyanoacrylic glue 44 to adhere and seal the edges of the appendicular aperture (not numbered) to the outside wall of tubing 12, the appendix attached to the tubing 12 is returned to its normal position in the test animal's abdomen and the linea alba is closed using a 3–0 absorbable suture in a simple interrupted pattern in conventional manner.

A subcutaneous tunnel is created by blunt dissection, extending from the abdominal incision to the dorsocervical neck disposed as indicated schematically in FIG. 1. The obturator end of the tubing 12 is routed through the tunnel to the dorsocervical neck. The obturator is held externally and the abdominal skin is then sutured using non-absorbable material in a simple interrupted pattern in conventional manner.

Any restraints used on the animal are then removed and the animal is then repositioned into ventral recumbency An encircling of 0 silk is placed around the injection port, i.e., at the receiving end of the tubing, and patency of the system is assured by injection of 2.0 cc of sterile saline through the skin and into the injection port.

The test animal is then recovered from anesthesia and is returned to its cage where small quantities of feed are offered for the first day post-operatively, with normal feed allowance by the third day. Water is provided ad libitum following surgery.

After the first day post-op, the tubing is inspected and is flushed through every other day by injecting 2.0 cc of sterile saline through the tubing and into the appendix.

Once the test animal has recovered from the surgery incidental to the implantation of the tubing, any desired liquid material may be injected through fitting 38 located on the animal's shoulder behind its head in known manner. Naturally, a series of such doses of a single or a plurality of liquid materials can be readily administered. Because sterile surgical techniques are used and because the materials utilized are of the type tolerated by a living organism, there is a very low likelihood of infections or complications arising. Thus, for example, polyethylene tubing may be chosen because of its ability to swell in the presence of low heat (to easily form the bulbous portion 24); it does not precipitate tissue reaction, it is pliable and therefore comfortable for the animal to have implanted within it, it is inexpensive and it is readily available. Other tubing materials having some or all of these qualities may also be available and utilized freely.

Since the delivery end 20 of the tubing must remain within the animal's appendix for the duration of the study, formation of the small bulbous portion 24 to serve as a cuff to prevent dislodgement of tubing 12 from appendix 18 is considered highly desirable if not essential for retention of the tubing within the appendix. Heating of the tube locally to construct the cuff or bulbous portion 24 is preferable over the use of silastic glue to form the retention collar, because the polyethylene tubing when enlarged due to local heating is smoother and is contiguous with the rest of the tubing, whereas a silastic glue droplet would not be as smoothly contiguous and could cause appendicular irritation and possible damage.

Cyanoacrylic glue is preferable for use at the tubing/appendix junction to assist in hemostasis and to provide stable fixation thereat. Caution must be exercised in applying the glue, however, as an excess may result in permanent attachment of the appendix to any other soft tissue that it touches during application and before curing of the glue. In tests, system failures were detected in the early stages and involved either slippage of the tubing 12 from the needle 28 or fibrous tissue obstruction of the obturator. The first problem was eliminated by tying off the tubing around the needle and to the incised vanes of the needle hub as described hereinabove. Obturator failure and subsequent hub plugging are believed to be related to subcutaneous implantation of a device not intended for implantation, and it is believed that this may be solved by covering the obturator, needle hub, and proximal catheter with silastic glue prior to implantation to render the system more water resistant. In such tests, no failures were detected at the tubing/appendix junction, nor were there any signs of peritonitis detected at necropsy of the test animals. Culture of the abdominal cavity, by swabbing serosal linings and free abdominal fluid, proved to be negative for growth of organisms at surgery and at necropsy. This is taken to indicate that there was no leakage from the inside of appendix 18 at the tubing appendix junction formed as taught herein.

When the invention is constructed and utilized as indicated hereinabove, a controlled flow of a selected liquid material flows as indicated by the arrow marked "F" in FIG. 3, directly into the appendix of the test animal, and comes into contact with the inside lining surface 40 of appendix 18. Since the rabbit has a relatively large appendix, this invention and the method of its use, by the use of readily available, inexpensive components makes it very easy for clinicians and researchers to conduct sensitive extended studies in mucosal administration of vaccines and the like.

While there has been described and illustrated one specific embodiment of the invention, it will be clear that variations in the details of the embodiment specifically illustrated and described may be made without departing from the true spirit and scope of the invention as defined in the appended claims

What is claimed is:

1. A device to provide multiple doses of a liquid material over an extended period of time to areas of the gastrointestinal tract consisting essentially of the small intestines, colon, stomach in gut-associated lymphoid tissue (GALT) of a test animal:
   (a) a length of tubing, formed to have a first end adapted to be affixed in fluid communication with a portion of the test animal's gastrointestinal tract contained within the test animal's body and an enlarged cross-section adjacent the first end to facilitate the securing of the affixation, the tubing having a second end adapted for receiving a quantity of a liquid material for delivery through the tubing to said gastrointestinal tract; and
   (b) means for affixing the first end in fluid communication with said gastrointestinal tract comprising a suture applied in a known purse-string manner about an opening formed at a selected portion of said GALT to the first end of the tubing projected therethrough and a quantity of adhesive material applied to adhere to the GALT and to the tubing to secure and seal said opening to the tubing projected therethrough, such that the second end is readily accessible by a user of the device but with the length of tubing between the first and second ends and the second end all being secured to be safe from dislocation and within the test animal.

2. A device according to claim 1, wherein: the affixing means comprises a suture applied in a known purse-string manner about an opening formed at a selected position of said GALT to the first end of the tubing projected therethrough.

3. A device according to claim 1, wherein: said affixing means comprises a quantity of adhesive material applied to adhere to the GALT and to the tubing to secure and seal the opening to the tubing projected therethrough.

4. A device according to claim 1, wherein the length of tubing between the first and second ends thereof is disposed to be under the animal's skin and the second end is located behind the test animal's head.

5. A device according to claim 1, wherein:
   the second end comprises a blunt-ended short needle in fluid communication with a needle hub of known type that is adapted to selectively connect with known means for providing a liquid material therethrough.

6. A device according to claim 5, wherein:
   the length of tubing between the first and second ends thereof is disposed to be under the animal's skin and the second end is located behind the test animal's head.

7. A device according to claim 6, wherein:
   the second end comprises a blunt ended short needle communicating with a needle hub of known type that is adapted to selectively connect with known means for providing a liquid material therethrough.

8. A device according to claim 6, wherein:
   the test animal is a rabbit and said first end is located inside the rabbit's appendix.

9. A method for delivering multiple doses of a liquid material over an extended period of time to areas within the gastrointestinal tract consisting essentially of the small intestines, colon stomach or a gut-associated lymphoid tissue (GALT) of a test animal, comprising the steps of:
   (a) affixing a first end of a length of tubing in fluid communication with a selected portion of the gastrointestinal tract within the test animal comprising the steps of accessing a portion of the test animal that contains the selected portion of the gastrointestinal tract, forming an aperture thereat, projecting the first end of the tubing therethrough, and connecting the tubing securely to the periphery of the apeture comprising the steps of applying a purse-string suture in known manner about the aperture around said tubing projected thereinto and applying an adhesive for securely adhering said aperture periphery to an outside surface of the tubing thereat;
   (b) flowing into the second end a dose of a liquid material, for conveyance thereof through the length of tubing and said first end to the gastrointestinal tract.

10. A method according to claim 1, wherein said securing step includes the steps of forming a subcutaneous tunnel extending from a first point near the first end of the tubing to a second point near the second end of the tubing, placing the tubing within the tunnel, and positioning the second end at said second point for convenient access thereto.

11. A method according to claim 1, wherein said securing step includes the steps of connecting said second end of said tubing to a blunt needle that has a fitting of known type and fixing the same securely behind the test animal's head 12. A method according to claim 1, wherein: said flowing step includes the steps of temporarily connecting a source of a liquid to said second end and generating a flow of the liquid from said source into said second end.

13. A method according to claim 1, comprising the further steps of:
   forming a portion of said tubing adjacent said first end into a smooth enlarged cross-section to facilitate said affixing step.

14. A method according to claim 1, wherein
said securing step includes the steps of forming a subcutaneous tunnel extending from a first point near the first end of the tubing to a second point near the second end of the tubing, placing the tubing within the tunnel, and positioning the second end at said second point for convenient access thereto.

15. A method according to claim 13, wherein:
said securing step includes the steps of forming a subcutaneous tunnel extending from a first point near the first end of the tubing to a second point near the second end of the tubing, placing the tubing within the tunnel, and positioning the second end at said second point for convenient access thereto.

16. A method according to claim 15, wherein
the test animal is a rabbit and said enlarged cross-section portion is located inside the rabbit's appendix.

* * * * *